United States Patent [19]

Alferness et al.

[11] Patent Number: 5,531,781

[45] Date of Patent: Jul. 2, 1996

[54] IMPLANTABLE LEAD HAVING A STEERING DISTAL GUIDE TIP

[76] Inventors: Clifton A. Alferness, 2022 235th Place NE., Redmond, Wash. 98053; John R. Helland, 2414 239th Place NE., Redmond, Wash. 98053; Paul Kreyenhagen, 5508 160th Avenue NE., Redmond, Wash. 98052

[21] Appl. No.: 145,716

[22] Filed: Nov. 2, 1993

[51] Int. Cl.$^6$ .................................................. A61N 1/05
[52] U.S. Cl. ........................ 607/122; 607/125; 607/126; 607/119; 128/642
[58] Field of Search .................................. 128/642, 772, 128/656, 657; 607/122, 125, 126, 119, 116, 117

[56] References Cited

U.S. PATENT DOCUMENTS

| | | | |
|---|---|---|---|
| 1,908,583 | 5/1933 | Wappler | 607/116 |
| 4,057,067 | 11/1977 | Lajos | 607/125 X |
| 4,402,328 | 9/1983 | Doring | 607/125 |
| 4,402,329 | 9/1983 | Williams | 607/125 |
| 4,677,990 | 7/1987 | Newhauer | 607/119 |
| 4,784,161 | 11/1988 | Skalsky et al. | 607/122 X |
| 4,813,429 | 3/1989 | Eshel et al. | 128/736 |
| 4,846,186 | 7/1989 | Box et al. | 128/772 X |
| 4,945,922 | 8/1990 | Van Krieken | 607/126 |
| 5,215,090 | 6/1993 | Hon et al. | 128/642 |
| 5,254,088 | 10/1993 | Lundquist et al. | 128/772 X |
| 5,360,441 | 11/1994 | Otten | 607/122 |
| 5,376,109 | 12/1994 | Lindegren et al. | 607/122 |

*Primary Examiner*—Krista M. Zele
*Assistant Examiner*—Brian Casler
*Attorney, Agent, or Firm*—Richard O. Gray, Jr.

[57] ABSTRACT

A lead is provided which assists in the implantation of the lead within an artery or vein of a human heart. The lead includes a lead body having a distal end and a proximal end and at least one electrode carried by the lead body intermediate the distal end and the proximal end. The lead includes a guide tip carried by the lead body which extends distally from the lead body distal end. The guide tip includes a distal tip end and a tapered portion forming the distal tip end. The tapered portion is curved in a direction of curvature to offset the distal tip end in a direction from the longitudinal center axis of the lead body. The guide tip may further include tines or fibrotic tissue ingrowth sites for retaining the lead in place after implantation.

58 Claims, 5 Drawing Sheets

IMPLANTABLE LEAD HAVING A STEERING DISTAL GUIDE TIP

BACKGROUND OF THE INVENTION

The present invention generally relates to an implantable intravenous or endocardial lead for use with an implantable cardiac device, such as an atrial defibrillator. The present invention is more particularly directed to such a lead which is implantable within a vein or artery of the heart and which includes a steerable tip at the distal end of the lead to enable the lead to be steered along a desired path as the lead is implanted. The steerable tip may also include fixation means for retaining the lead within the artery or vein.

Implantable cardiac devices, such as pacemakers or defibrillators, are well known in the art. Such devices are configured to be implanted within a subcutaneous pocket beneath the skin of a patient and to be electrically coupled to the heart through one or more leads also implanted beneath the skin of the patient. Each lead includes at least one electrode which, when properly positioned within the heart or within a vein or artery of the heart, makes electrical contact with a desired portion of the heart for either sensing heart activity or applying a therapeutic electrical stimulus to the heart.

One such implantable cardiac device is an atrial defibrillator of the type, for example, described and shown in U.S. Pat. No. 5,207,219 which issued on May 4, 1993 in the names of John M. Adams, Clifton A. Alferness, Kenneth R. Infinger, and Joseph M. Bocek for "Atrial Defibrillator and Method for Providing Interval Timing Prior to Cardioversion", which patent is assigned to the assignee of the present invention and incorporated herein by reference. The atrial defibrillator described in that patent utilizes a first electrode positioned in the right atrium or superior vena cava of the heart and a second electrode positioned in the coronary sinus and great cardiac vein of the heart adjacent the left atrium. When the atria are in need of cardioversion, the atrial defibrillator applies cardioverting electrical energy between the first and second electrodes to cardiovert the atria.

The cardioverting pathway between the right atrium or superior vena cava and the coronary sinus and great cardiac vein has been shown to exhibit distinct advantages over previous pathways for cardioverting the atria. For example, by cardioverting the atria between the right atrium or superior vena cava and the coronary sinus and great cardiac vein, the cardioverting electrical energy is confined, in large measure, to the atria. This reduces the risk of undesirable side effects such as the inducement of ventricular fibrillation during atrial cardioversion. Also, it has been further found that this pathway reduces the energy levels required to cardiovert the atria resulting in less discomfort to the patient and less energy consumption by the defibrillator to thus extend its useful life.

One problem associated with the above-mentioned pathway is that it can be difficult to implant a lead for positioning an electrode within the coronary sinus and great cardiac vein. One method for implanting the lead and electrode, and as described in the aforementioned reference patent, includes passing the lead down the superior vena cava, through the right atrium, through the os or ostium (opening to the coronary sinus) and around to and into the great cardiac vein. This route unavoidably requires the lead distal end to be maneuvered around corners, past vein branches, and across constrictions in the coronary sinus and great cardiac vein.

Unfortunately, prior art leads do not incorporate any means to enable such corners, branches, or constrictions to be negotiated. Further, prior art leads have distal ends which are blunt and thus inherently difficult to properly implant and position. This is indeed unfortunate because if an electrode is not properly positioned, the intended therapy, whether pacing or cardioverting, can be severely compromised or even rendered ineffective altogether.

A further aspect of lead implantation, and particularly in the context of an intravenous lead such as one intended to position an electrode in the coronary sinus and great cardiac vein, is that the lead must also provide a means by which the lead, and hence the electrode, may be retained in the proper position. In the case of a coronary sinus and great cardiac vein electrode carrying lead, this is of great importance because the direction of blood flow through the coronary sinus is opposite to the direction of lead implantation. Hence, the blood flow through the coronary sinus tends to push the lead out of the coronary sinus, thereby resulting in lead dislodgement, rendering the lead nonfunctional.

One effective solution to this problem is fully described in co-pending U.S. patent application Ser. No. 08/002,138, filed Jan. 11, 1993 in the name of Clifton A. Alferness for "Coronary Channel Lead with Improved Fixation and Method", which application is also assigned to the assignee of the present invention and incorporated herein by reference. In accordance with one embodiment described in that application, the body of the lead is provided with a preformed resilient coiled configuration which, when released after implantation, expands to make continuous surface contact with inner wall surfaces of the artery or vein in which the lead is implanted. This serves to positively retain the lead in position while still providing a sufficient channel for blood flow through the coronary sinus.

Notwithstanding such an elegant solution for lead retention, alternative lead retention means may further be desirable. However, such lead retention means should not interfere with or otherwise hamper the implantation of the lead.

The present invention provides an endocardial or intravenous lead which successfully addresses each of the above-mentioned deficiencies of the prior art. The lead of the present invention includes a distal guide tip which, upon rotation of the body of the lead during implantation, serves to steer the distal tip end of the lead in a desired direction to readily negotiate corners, branches, and constrictions or the like. Further, the lead of the present invention includes fixation means formed in the distal guide tip for positively retaining the lead in its final position without impeding the implantation process.

SUMMARY OF THE INVENTION

The present invention therefore provides an electrode carrying lead for implantation within an artery or vein of a human heart. The lead includes a longitudinal center axis, a distal end, a proximal end, and a guide tip. The guide tip is positioned at the distal end and includes a tip end. The guide tip includes a tapered portion forming the tip end and the tip end is offset in a direction from the lead body longitudinal center axis.

The present invention further provides a lead for implantation within an artery or vein of a human heart. The lead includes a lead body having a distal end and a proximal end, at least one electrode carried by the lead body intermediate the distal end and the proximal end, and a guide tip carried by the lead body. The guide tip extends distally from the lead body distal end and includes a distal tip end. The guide tip includes a tapered portion to form the distal tip end and the tapered portion is curved in a direction of curvature.

The guide tip may further include fixation means for retaining the lead within the artery or vein.

The present invention still further provides a lead for implantation within an artery or vein of a human heart wherein the lead includes a lead body having a distal end and a proximal end, at least one electrode carried by the lead body intermediate the distal end and the proximal end, and a guide tip formed of electrically insulating material carried by the lead body. The guide tip extends distally from the lead body distal end and includes a distal tip end, a tapered portion to form the distal tip end, and fixation means for retaining the lead within the artery or vein.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements and wherein:

DESCRIPTION OF THE PREFERRED EMBODIMENTS

Figure 1:
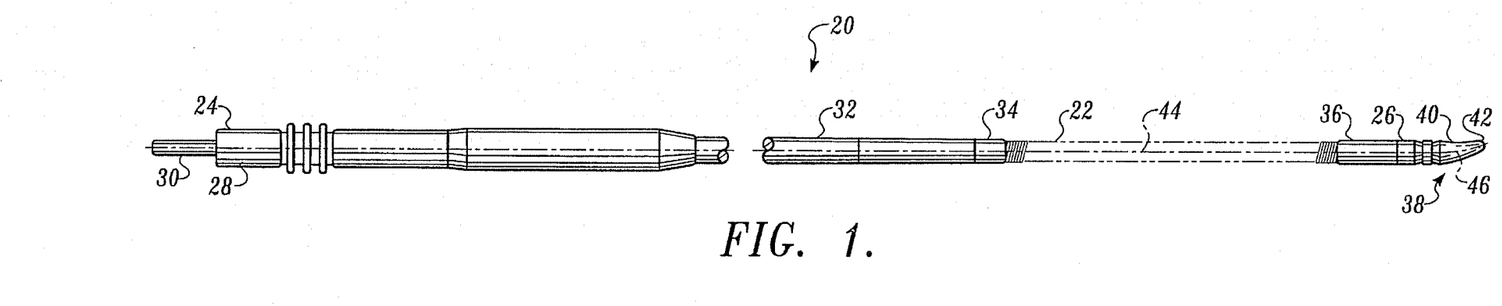
FIG. 1 is a side plan view of an implantable lead having a steerable distal guide tip embodying the present invention.

Referring now to FIG. 1, it illustrates an implantable lead 20 embodying the present invention. The lead 20 is particularly configured for use with an implantable atrial defibrillator for placing a coiled electrode 22 in the coronary sinus and great cardiac vein of the heart. In addition to the electrode 22, the lead 20 includes a proximal end 24 and a distal end 26. At the proximal end 24 is a connector 28 having a connector pin 30 for connecting the electrode 22 to an implantable atrial defibrillator (not shown). The electrode 22 is carried by a lead body 32 which extends from the proximal end 24 to the distal end 26. The electrode 22 is secured to the lead body at its proximal end by a proximal electrode header 34 and at its distal end by a distal electrode header 36.

The lead 20 further includes a guide tip 38 structured in accordance with the present invention. The guide tip is carried by the lead body 32 and extends distally from the lead body distal end 26. The guide tip includes a tapered portion 40 which converges to form a distal tip end 42.

As will be noted in FIG. 1, the tapered portion 40 is curved in a direction of curvature. More specifically, the lead body 32 of lead 20 includes a center longitudinal axis 44. The guide tip 38 in turn includes a center axis 46. As will be noted in FIG. 1, the center axis 46 of the guide tip 38 is curved away from the longitudinal center axis 44 of the lead body 32 so that the distal tip end 42 of the guide tip 38 is offset in the direction of curvature from the longitudinal center axis 44 of the lead body 32.

Because the guide tip 38 is curved with the tip end 42 offset from the longitudinal center axis 44 of lead body 32 as illustrated, the guide tip 38 is steerable for steering the lead 20 during implantation. The lead body 32 preferably includes a hollow core which receives a stylet during implantation. When the lead body 32 is rotated about the stylet, it will be seen that the distal tip end 42 will rotate about the longitudinal center axis 44 of the lead body 32 so as to steer the distal end 26 of the lead 20. This enables the lead to be steered around corners, past vein branches, and across constrictions, such as in the coronary sinus and great cardiac vein, when the lead 20 is implanted.

The guide tip 38 may be formed from a rigid material. Preferably, such a rigid material is rigid porous material such as ceramic or a porous metal such as platinum or titanium. Such porous materials create sites for fibrotic tissue ingrowth to contribute to fixation of the lead 20 after being implanted.

The guide tip 38 may also be formed of a flexible or pliant material. Such materials include polymeric materials such as silicone rubber or polyurethane.

Figure 2:
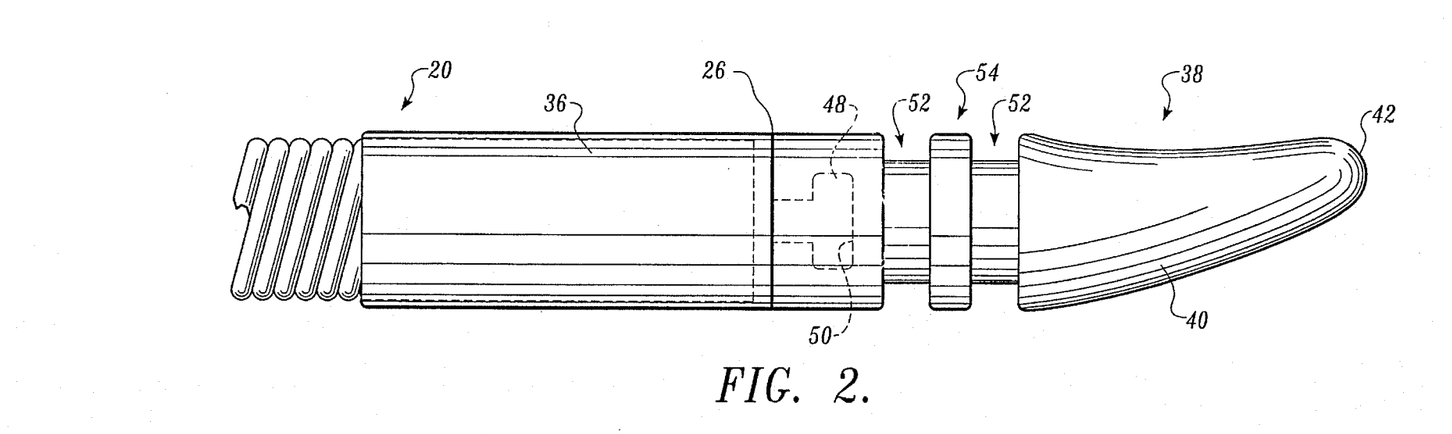
FIG. 2 is a partial side plan view, to an enlarged scale, of the distal end of the lead of FIG. 1.

Referring now to FIG. 2, it illustrates in a partial side plan view, the distal end of the lead 20 of FIG. 1. In FIG. 2 it can be seen that the distal electrode header 36 includes a retaining flange 48 which is received by a correspondingly shaped cavity 50 formed in the proximal end of the guide tip 38. This fixes the guide tip 38 to the distal end 26 of the lead 20. To that end, the guide tip 38 may be preformed with the cavity 50 for receiving the retaining flange 48 of the distal electrode header 36. Alternatively, if the guide tip 38 is formed of a moldable material, it may be molded onto the retaining flange 48.

The guide tip 38, as will be noted in FIG. 2, further includes a plurality of circumferential grooves 52. The grooves 52 form a fixation means 54 for receiving therein fibrotic tissue for retaining the lead 20 in place after implantation.

Figure 3:
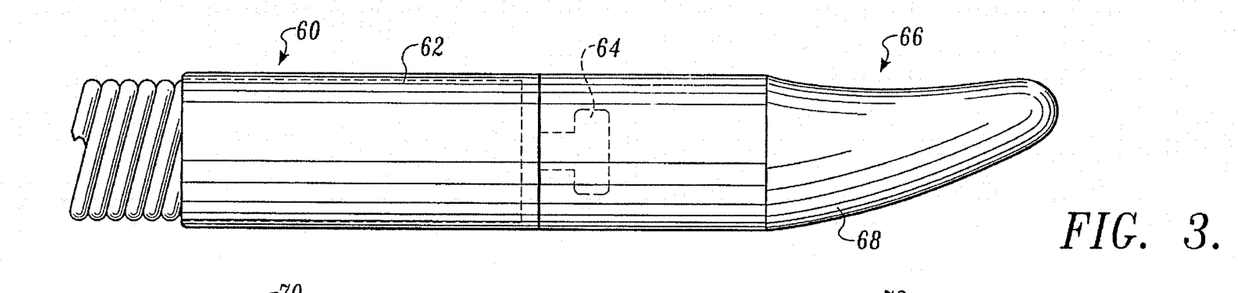
FIG. 3 is a partial side plan view, to an enlarged scale, of the steerable distal guide tip end of another lead embodying the present invention.

Referring now to FIG. 3, it shows the distal end of another lead 60 embodying the present invention. Like the lead 20 of FIGS. 1 and 2, the lead 60 includes a distal electrode header 62 having a retaining flange 64. A guide tip 66 having a curved tapered portion 68 is affixed to the retaining flange 64. Preferably, although not essential, the guide tip 66 is formed of one of the aforementioned porous rigid materials to provide fixation of the lead 60 after implantation. However, the lead 60 may be provided with other fixation means such as the fixation means disclosed in the aforementioned co-pending U.S. application Ser. No. 08/002,138.

Figure 4:
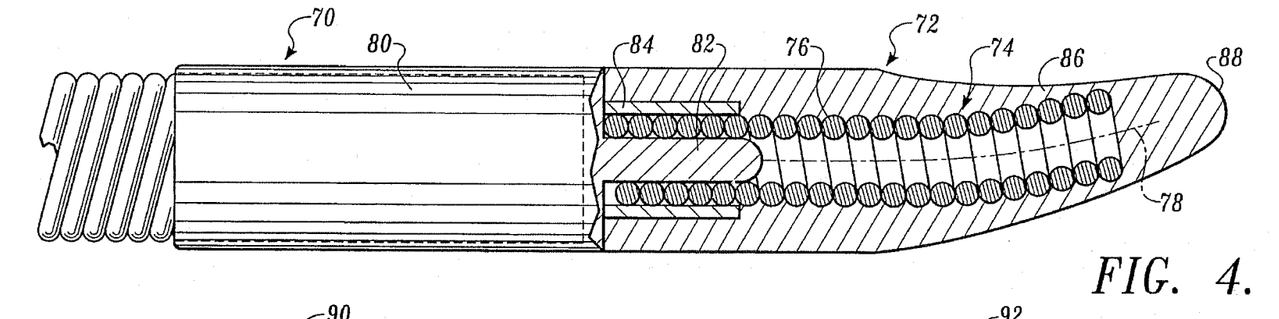
FIG. 4 is a partial side plan view, to an enlarged scale, of the steerable distal guide tip end of another lead embodying the present invention wherein the steerable guide tip includes a stiffening coiled spring.

Referring now to FIG. 4, it illustrates the distal end of another lead 70 embodying the present invention. The lead 70 includes a guide tip 72 which is similar in configuration to the guide tip 66 illustrated in FIG. 3. However, the lead 70 further includes a stiffening means 74 in the form of a coiled spring 76 for stiffening the guide tip 72. The coiled spring 76 has a longitudinal center axis 78. Preferably, the coiled spring 76 is positioned within the guide tip 72 so that the longitudinal center axis 78 of the coiled spring 76 substantially coincides with the center axis of the guide tip 72.

For retaining the guide tip 72 onto the lead 70, the distal electrode header 80 includes a cylindrically configured extension 82 having an outer diameter which lockingly receives the coiled spring 76. About the coiled spring 76 is a crimp ring 84 which may be crimped so as to retain the coiled spring on the cylindrically shaped projection 82 of the distal electrode header 80.

As in the previous embodiments, the guide tip 72 includes a tapered portion 86. The tapered portion 86 is curved and converges to form the distal tip end 88.

Figure 5:
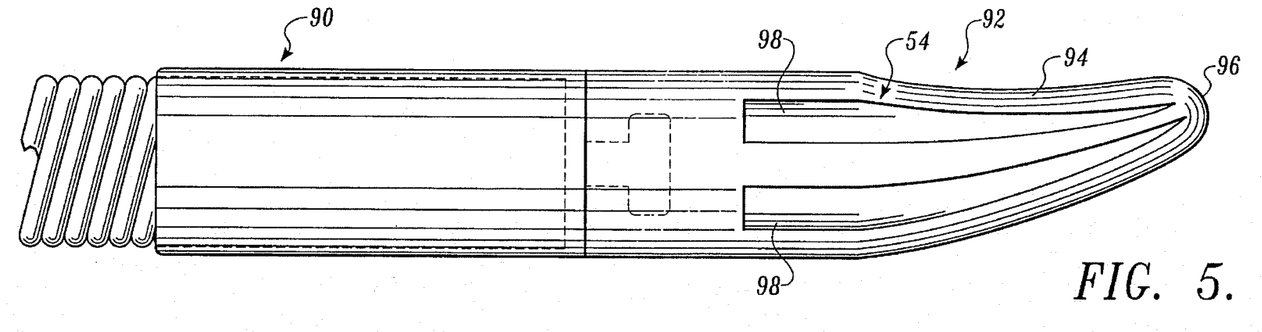
FIG. 5 is a partial side plan view, to an enlarged scale, of the steerable distal guide tip end of another lead embodying the present invention wherein the steerable guide tip includes longitudinal grooves for lead fixation.

Referring now to FIG. 5, it illustrates the distal end of another lead 90 embodying the present invention. The distal end of lead 90 is essentially identical in configuration to the distal end of lead 60 of FIG. 3. The guide tip 92 of lead 90 thus similarly includes a tapered portion 94 which is curved and converges to form a distal tip end 96. In contrast to the guide tip 66 of FIG. 3, the guide tip 92 of FIG. 5 includes fixation means 54 in the form of a plurality of longitudinal grooves 98 which are formed in the guide tip 92. The longitudinal grooves 98 provide ingrowth sites for fibrotic tissue for retaining the lead 90 in place after implantation.

Figure 6:
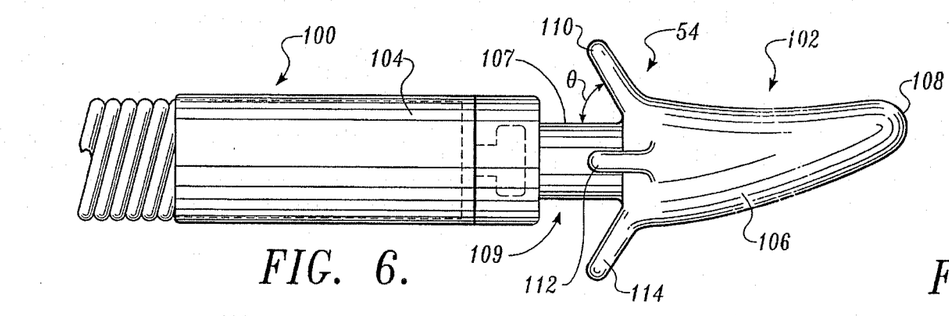
FIG. 6 is a partial side plan view, to an enlarged scale, of the steerable distal guide tip end of another lead embodying the present invention wherein the guide tip includes a plurality of tines for lead fixation.

Referring now to FIG. 6, it illustrates the distal end of a further lead 100 embodying the present invention. As in the previous embodiments, the distal end of lead 100 includes a guide tip 102 which is retained and carried by the distal electrode header 104 in a manner as previously described. The guide tip 102 also includes a tapered portion 106 which is curved and converges to form the distal tip end 108.

The guide tip 104 also includes fixation means 54 in the form of a plurality of tines 110, 112, 114, and 116. The tines are equally spaced about the guide tip 102 and project proximally from the guide tip 102 and at an acute angle $\Theta$ from the guide tip 102.

Figure 7:
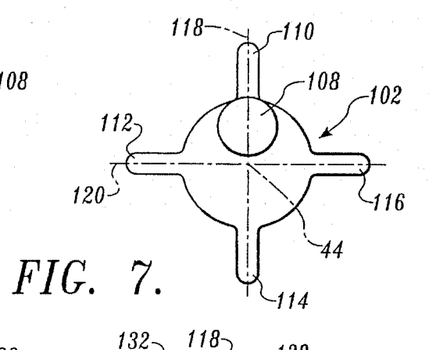
FIG. 7 is an end view of the lead distal end of FIG. 6.

As may be best seen in FIG. 7, the distal tip end 108 is displaced from the longitudinal center axis 44 of the lead 100 and hence the tapered portion 106 is curved in a direction of curvature within a first plane 118. The tines 112 and 116 project from the guide tip 102 in a second plane 120 which is orthogonal to the first plane 118.

Preferably, in accordance with this embodiment, the guide tip 102 is formed of a pliant or flexible material. Also preferably, the tines 110, 112, 114, and 116 are integrally formed with the guide tip 102 so that the tines are also flexible and pliant. A reduced diameter portion 107 of the guide tip 102 forms a space 109 for receiving the tines as they are deflected in a proximal direction toward axis 44 (FIG. 7) during implantation of the lead 100. The tines preferably are relatively short and small in cross-sectional dimension as compared to the tines of prior art pacing endocardial leads, each tine having a length less than two millimeters, and preferably about one millimeter, and a cross-sectional major dimension less than one-half millimeter, and preferably about one-fourth millimeter. Further, the tines need not necessarily be circular in cross-section.

Because the tines are flexible and pliant and because the tines may be received into the space 109 formed by the reduced diameter portion 107 during implantation of the lead 100, the tines will not interfere with or impede the steering or implantation of the lead 100. However, once the lead is properly positioned within an artery or vein, the tines will be effective, due to their relatively short length, to spring back either partially or fully into the configuration illustrated to engage the inner wall of the artery or vein. This will promote the growth of fibrotic tissue about the tines for retaining the lead 100 in place.

Figure 8:
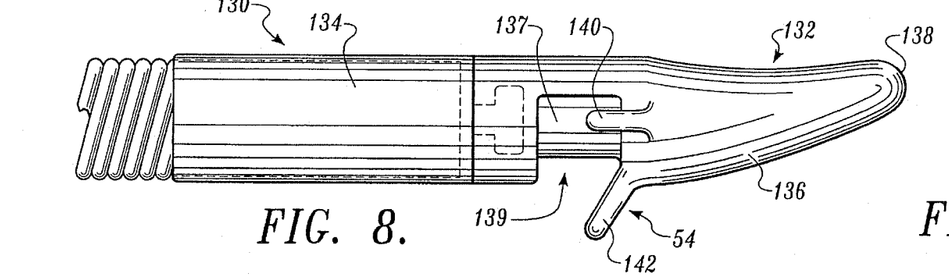
FIG. 8 is a side plan view, to an enlarged scale, of the steerable distal guide tip end of another lead embodying the present invention wherein the guide tip includes a plurality of tines arranged to assist the guide tip in steering the lead during implantation and for lead fixation in accordance with further aspects of the present invention.

Referring now to FIG. 8, it shows the distal end of a further lead 130 embodying the present invention. The lead 130 includes a guide tip 132 which, in accordance with previous embodiments, is retained and carried by the distal electrode header 134. Also in accordance with previous embodiments, the guide tip 132 includes a tapered portion 136 which is curved and converges to form the distal tip end 138.

Figure 9:
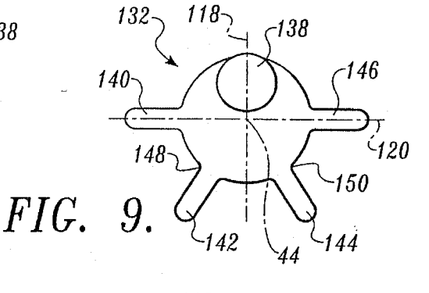
FIG. 9 is an end view of the lead distal end of FIG. 8.

As may be best seen in FIG. 9, the guide tip 132 includes fixation means 54 in the form of tines 140, 142, 144, and 146. The tines 140, 142, and 144 may have the same dimensions as the tines of FIGS. 6 and 7 and may be received within a space 139 formed by a reduced diameter portion 137 during implantation. As will be noted in FIG. 9, the distal tip end 138 is displaced or offset from the longitudinal center axis 44 of the lead 130 in a direction within the plane 118. Tines 142 and 144 extend from the guide tip 132 from points 148 and 150 which are below the second plane 120 which is orthogonal to the first plane 118. Because all of the tines 140, 142, 144, and 146 extend from the guide tip 136 either within the plane 120 or below the plane 120 with respect to the direction of curvature of the tapered portion 136 and hence the direction of offset of the distal tip end 138 from the longitudinal center axis 44 of the lead 130, the tines, in addition to the function described with reference to FIGS. 6 and 7, will also assist the curved tapered portion 136 in steering the lead as the lead is rotated during implantation, and push the distal portion of the lead against the inner walls of the artery or vein after implantation to promote retention of the lead by enhancing the development of fibrotic tissue.

Figure 10:
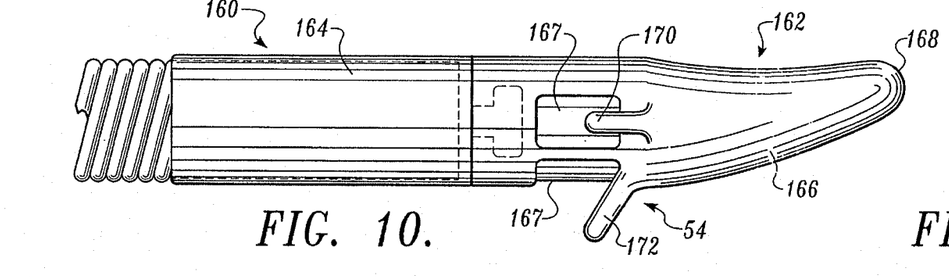
FIG. 10 is a side plan view, to an enlarged scale, of the steerable distal guide tip end of a further lead embodying the present invention wherein the guide tip includes three tines for lead fixation in accordance with further aspects of the present invention.

Referring now to FIG. 10, it illustrates the distal end of a further lead 160 embodying the present invention. The lead 160 includes a guide tip 162 which is retained and carried by the distal electrode header 164 in a manner previously described. The guide tip 162 includes a tapered portion 166 which is tapered and converges to form the distal tip end 168. The guide tip 162 also includes fixation means 54 which, as may be best seen in FIG. 11, includes tines 170, 172, and 174 which may be dimensioned as previously described. During implantation of lead 160, the tines 170, 172, and 174 may be received within recesses 167 formed in the guide tip 162.

Figure 11:
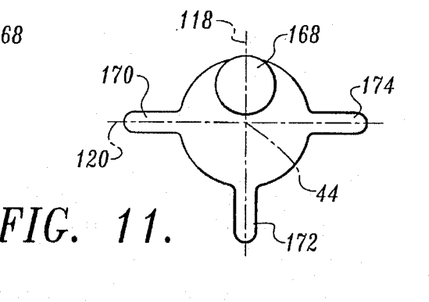
FIG. 11 is an end view of the lead distal end of FIG. 10.

As will also be seen in FIG. 11, the tine 172 is disposed within the first plane 118 and extends in a direction opposite the direction of offset of the distal tip end 168 from the longitudinal center axis 44 of the lead 160. Tines 170 and 174 are disposed on respective opposite sides of tine 172, are equally spaced from tine 172, and lie within the second plane 120 which is orthogonal to the first plane 118. Hence, the tines 170, 172, and 174 will perform all of the functions as the tines of FIGS. 8 and 9.

Figure 12:
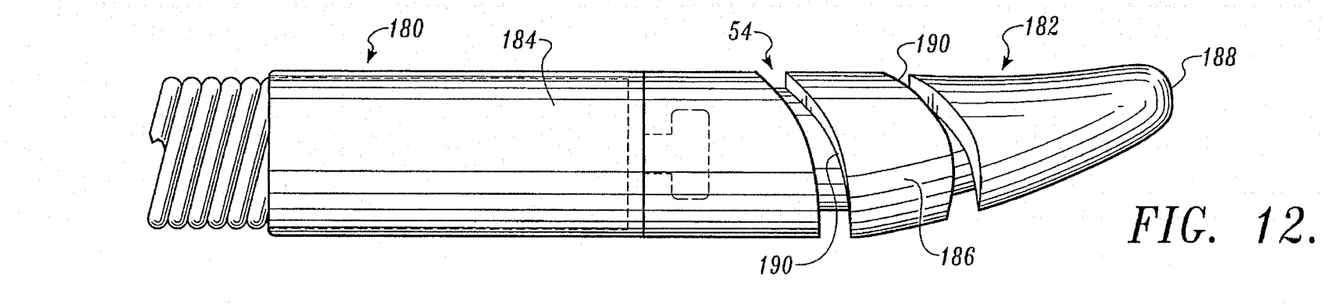
FIG. 12 a side plan view, to an enlarged scale, of the steerable distal guide tip end of another lead embodying the present invention wherein the guide tip includes a continuous spiral groove for lead fixation in accordance with a further aspect of the present invention.

Referring now to FIG. 12, it illustrates the distal end of another lead 180 embodying the present invention. The lead 180 includes a guide tip 182 which, in accordance with previous embodiments, is retained and carried by the distal electrode header 184. Also in accordance with the previous embodiments, the guide tip 182 includes a tapered portion 186 which is curved and converges to form a distal tip end 188. The guide tip 182 includes fixation means 54 in the form of a continuous spiral groove 190. The spiral groove 190 provides sites for ingrowth of fibrotic tissue for retaining the lead 180 in place after implantation.

Figure 13:
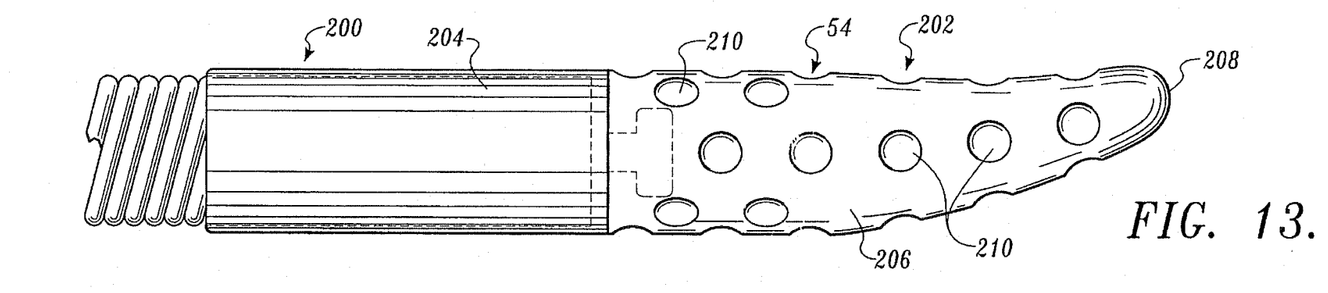
FIG. 13 is a side plan view, to an enlarged scale, of the steerable distal guide tip end of a further lead embodying the present invention wherein the guide tip includes a plurality of indentations for lead fixation in accordance with a further aspect of the present invention.

Referring now to FIG. 13, it illustrates the distal end of a further lead 200 embodying the present invention. The lead 200 includes a guide tip 202 which, in accordance with previous embodiments, is carried and retained by the distal electrode header 204. The guide tip 202 includes a tapered portion 206 which is curved and converges to form a distal tip end 208. The guide tip 202 includes fixation means 54 in the form of a plurality of indentations 210 which are formed in the guide tip 202 and which imparts an irregular surface to the guide tip 202. The irregular surface provided by the indentations provides ingrowth sites for fibrotic tissue for retaining the lead 200 in place after implantation. Alternatively, the irregular surface of the guide tip 202 may be provided by multiple bumps or protrusions formed in the guide tip 202 or by small particles of granulated material adhered to the surface of the guide tip 202. Each of these structures would provide sites for fibrotic tissue growth for lead retention.

Figure 14:
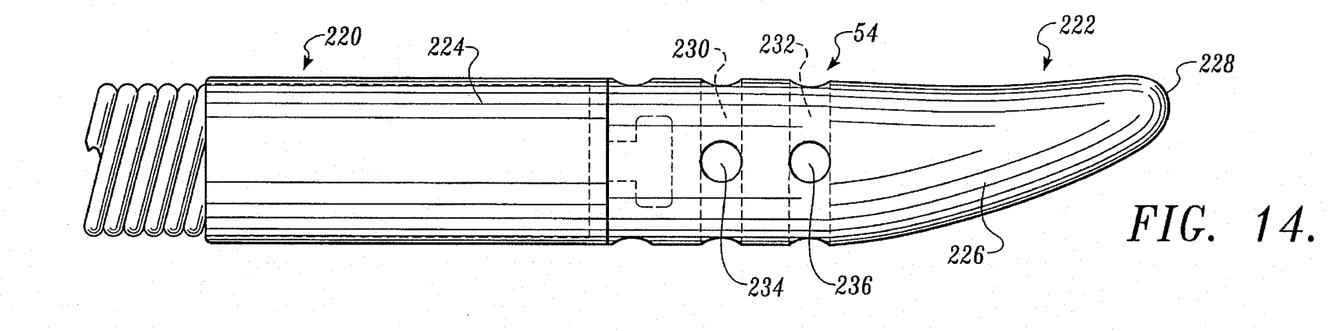
FIG. 14 is a side plan view, to an enlarged scale, of the steerable distal guide tip end of another lead embodying the present invention wherein the guide tip includes a plurality of through-holes for lead fixation.

Referring now to FIG. 14, it illustrates the distal end of a further lead 220 embodying the present invention. The lead 220 includes a guide tip 222 which is carried and retained by the distal electrode header 224. The guide tip 222 includes a tapered portion 226 which is curved and converges to form the distal tip end 228. The guide tip 222 includes fixation means 54 in the form of a plurality of through-holes 230, 232, 234, and 236. The through-holes extend entirely through the guide tip 222 as illustrated. The through-hole 230 is orthogonal to and intersects the through-hole 234. Similarly, the through-hole 232 is orthogonal to and intersects the through-hole 236. The through-holes 230, 232, 234, and 236 provide ingrowth sites for fibrotic tissue for retaining the lead 220 in place after implantation.

Figure 15:
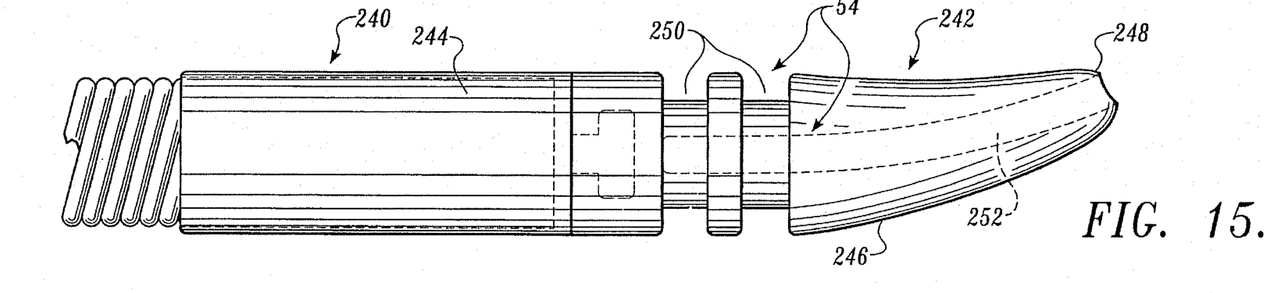
FIG. 15 is a side plan view, to an enlarged scale, and partly in cross-section, of the steerable distal guide tip end of a further lead embodying the present invention wherein the guide tip includes a plurality of circumferential grooves and a longitudinal bore for lead fixation.

Referring now to FIG. 15, it illustrates the distal end of a still further lead 240 embodying the present invention. The lead 240 includes a guide tip 242 which is carried and retained by the distal electrode header 244. The guide tip 242 includes a tapered portion 246 which is curved and converges to form the distal tip end 248. The guide tip 242 includes retaining means 54 in the form of a plurality of circumferential grooves 250 and a longitudinal bore 252 formed in the guide tip 242. The circumferential grooves 250 and the longitudinal bore 252 provide ingrowth sites for fibrotic tissue for retaining the lead 240 in place after implantation.

Figure 16:
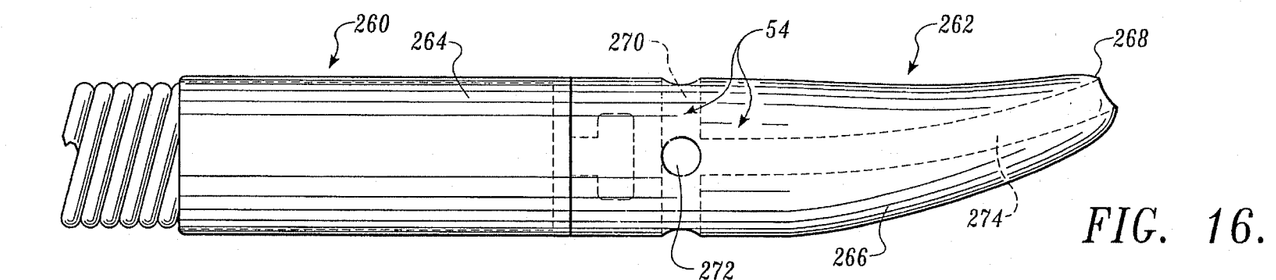
FIG. 16 is a side plan view, to an enlarged scale, of the steerable distal guide tip end of another lead embodying the present invention wherein the guide tip includes a through-hole and a longitudinal bore for lead fixation.

Referring now to FIG. 16, it illustrates the distal end of a further lead 260 embodying the present invention. The lead 260 includes a guide tip 262 which is carried and retained by the distal electrode header 264. The guide tip 262 includes a tapered portion 266 which is curved and converges to form the distal tip end 268. The guide tip 262 includes fixation means 54 including a first through-hole 270, a second through-hole 272, and a longitudinal bore 274. The through-hole 270 is orthogonal to and intersects the second through-hole 272. The longitudinal bore 274 also intersects the through-holes 270 and 272. As a result, the through-holes 270 and 272 and the longitudinal bore 274 provide ingrowth sites for fibrotic tissue to retain the lead 260 in place after implantation.

Figure 17:
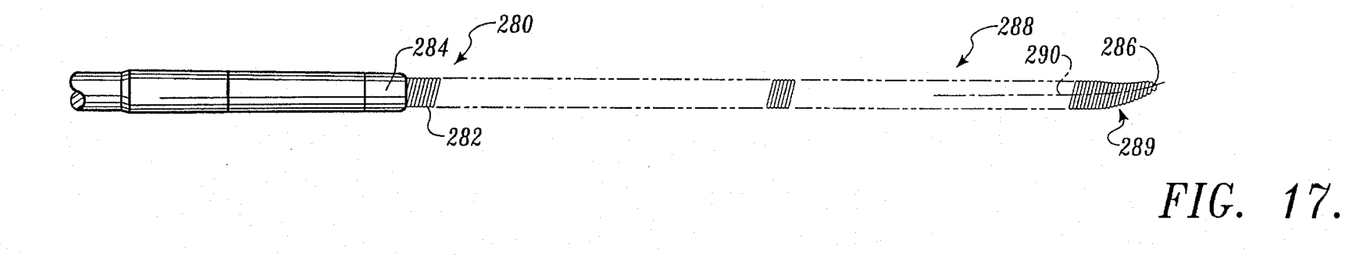
FIG. 17 is a partial side plan view of another lead embodying the present invention.

Referring now to FIG. 17, it illustrates, in partial side plan view, another lead 280 embodying the present invention. The lead 280 is an elongated electrode 282 which extends from an electrode header 284 to the tip end 286 of the lead distal end 288. As will be noted from FIG. 17, the elongated electrode comprises a coil electrode which is shaped to form the guide tip 289. Hence, the electrode 282 is shaped at the distal end 288 to form a tapered portion 290 which is curved and converges to form the distal tip end 286 so that the distal tip end 286 is offset from the longitudinal center axis of the lead 280. The irregular surface of the electrode 282 resulting from the coil turns of the electrode provide ingrowth sites for fibrotic tissue for retaining the lead 280 in place after implantation.

From the foregoing, it can be seen that the present invention provides a new and improved implantable lead for use with an implantable cardiac device. More particularly, the present invention provides a new and improved lead for implantation within an artery or vein of the heart. The new and improved lead includes a guide tip having a distal tip end which is offset from the longitudinal central axis of the lead body to permit the guide tip to steer the lead body as the lead body is rotated during implantation. Preferably, the guide tip is curved in configuration and includes a tapered portion for forming the distal tip end. As a result, the new and improved lead of the present invention is capable of negotiating corners, branches, or constrictions which may be encountered during the implantation of such a lead in an artery or vein such as the coronary sinus and great cardiac vein of the heart.

In addition to the foregoing, the new and improved lead includes fixation means for retaining the lead in place after implantation. The fixation means as disclosed herein do not interfere or otherwise impede the steerability of the guide tip and hence the implantation of the lead. In fact, in accordance with the embodiment of FIGS. 8 and 9 and 10 and 11, the fixation means add to the steerability of the lead distal end.

As a result, the new and improved lead of the present invention provides a means by which an electrode carried by the lead may be properly positioned within the desired location of an artery or vein of the heart. Hence, the intended pacing or defibrillation therapy to be derived from the positioned electrode will be neither severely compromised nor rendered ineffective.

While particular embodiments of the present invention have been shown and described, modifications may be made, and it is therefore intended in the appended claims to cover all such changes and modifications which may fall within the true spirit and scope of the invention.

What is claimed is:

1. A lead for implantation within an artery or vein of a human heart, said lead including a lead body having a longitudinal hollow core defining a longitudinal center axis and dimensioned for receiving a styler during implantation, a distal end, and a proximal end, an electrode affixed to said lead body and coaxially disposed with respect to said longitudinal center axis on said lead body and a guide tip positioned at said distal end of said lead body and including a tip end, said guide tip including a tapered portion forming said tip end wherein only said tip end is offset in a direction from said lead body longitudinal center axis so that when said lead body is rotated about a stylet during implantation, said tapered portion of said guide tip serves to steer the distal end of said lead body.

2. A lead as defined in claim 1 wherein said tapered portion includes a central axis, said central axis being curved away from said lead longitudinal center axis.

3. A lead as defined in claim 1 wherein said guide tip is formed of a rigid material.

4. A lead as defined in claim 1 wherein said guide tip is formed of a rigid porous material.

5. A lead as defined in claim 4 wherein said rigid material is one of ceramic and porous metal.

6. A lead as defined in claim 1 wherein said guide tip is formed of flexible material.

7. A lead as defined in claim 6 wherein said flexible material is a polymeric material.

8. A lead as defined in claim 6 wherein said flexible material is one of silicone and polyurethane.

9. A lead as defined in claim 6 further including stiffening means within said guide tip for stiffening said guide tip.

10. A lead as defined in claim 9 wherein said stiffening means comprises a coiled spring.

11. A lead as defined in claim 10 wherein said coiled spring has a longitudinal center axis and wherein said longitudinal axis of said coiled spring is substantially coincident with a central axis of said guide tip.

12. A lead as defined in claim 1 wherein said guide tip further includes fixation means for retaining said lead within the artery or vein.

13. A lead as defined in claim 12 wherein said fixation means comprises a plurality of grooves formed in said guide tip.

14. A lead as defined in claim 13 wherein said plurality 2 of grooves comprise circumferential grooves formed in said guide tip.

15. A lead as defined in claim 12 wherein said fixation means comprises a plurality of longitudinal grooves formed in said lead body.

16. A lead as defined in claim 12 wherein said fixation means comprises a spiral groove formed in said guide tip.

17. A lead as defined in claim 12 wherein said fixation means comprises a first through-hole extending entirely through said guide tip.

18. A lead as defined in claim 17 wherein said fixation means includes a second through-hole extending entirely through said guide tip and wherein said first and second through-holes are orthogonal to one another.

19. A lead as defined in claim 12 wherein said fixation means comprises a longitudinal bore formed in said guide tip.

20. A lead as defined in claim 19 wherein said fixation means further includes a through-hole extending entirely through said guide tip and intersecting said longitudinal bore.

21. A lead as defined in claim 12 wherein said fixation means comprises an irregular surface of said guide tip.

22. A lead as defined in claim 21 wherein said irregular surface comprises a plurality of indentations formed in said guide tip.

23. A lead as defined in claim 12 wherein said fixation means comprises a plurality of tines extending proximally from said guide tip and at an angle to said guide tip, said tines being formed of flexible material.

24. A lead as defined in claim 23 wherein each said tine has a length less than two millimeters and a major cross-sectional dimension of less than one-half millimeter.

25. A lead as defined in claim 23 wherein said plurality of tines comprise four tines equally spaced about said guide tip.

26. A lead as defined in claim 23 wherein said plurality of tines comprise a first tine, a second tine, and a third tine, said first tine extending in a direction substantially opposite to the direction of offset of said tip end from said lead body center axis and said second and third tines being disposed on respective opposite sides of said first tine.

27. A lead as defined in claim 26 wherein said second and third tines are equally spaced from said first tine.

28. A lead as defined in claim 27 wherein said second and third tines are in a common plane substantially perpendicular to the direction of offset of said tip end from said lead body center axis.

29. A lead as defined in claim 23 wherein said direction of offset is within a first plane, and wherein at least two of said plurality of tines extend from said guide tip from a point below a second plane orthogonal to said first plane.

30. A lead as defined in claim 29 wherein said plurality of tines consists of four tines.

31. A lead as defined in claim 1 further including an elongated electrode, said elongated electrode extending to said tip end and being shaped to form said guide tip.

32. A lead as defined in claim 31 wherein said elongated electrode comprises a coil electrode.

33. A lead for implantation within an artery or vein of a human heart, said lead comprising:

a lead body having a distal end and a proximal end;

at least one electrode coaxially disposed on said lead body intermediate said distal end and said proximal end; and a guide tip carried by said lead body, said guide tip extending distally from said lead body distal end and including a distal tip end, said guide tip including a tapered portion to form said distal tip end wherein only said tapered portion is curved in a direction of curvature.

34. A lead as defined in claim 33 wherein said guide tip is formed of rigid material.

35. A lead as defined in claim 34 wherein said rigid material is rigid porous material.

36. A lead as defined in claim 35 wherein said rigid porous material is one of ceramic and porous metal.

37. A lead as defined in claim 33 wherein said guide tip is formed of flexible material.

38. A lead as defined in claim 37 wherein said flexible material is a polymeric material.

39. A lead as defined in claim 37 further including stiffening means within said guide tip for stiffening said guide tip.

40. A lead as defined in claim 39 wherein said stiffening means comprises a coiled spring.

41. A lead as defined in claim 33 wherein said guide tip further includes fixation means for retaining said lead within the artery or vein.

42. A lead as defined in claim 41 wherein said fixation means comprises a plurality of tines extending proximally from said guide tip and at an acute angle from said guide tip, said tines being formed of flexible material.

43. A lead as defined in claim 42 wherein said plurality of tines comprises four tines equally spaced about said guide tip.

44. A lead as defined in claim 42 wherein said plurality of tines comprise a first tine, a second tine, and a third tine, said first tine extending in a direction substantially opposite to said direction of curvature of said guide tip and said second and third tines being disposed on respective opposite sides of said first tine.

45. A lead as defined in claim 44 wherein said second and third tines are equally spaced from said first tine.

46. A lead as defined in claim 45 wherein said second and third tines are in a common plane substantially perpendicular to said direction of curvature of said guide tip.

47. A lead as defined in claim 42 wherein said direction of curvature is within a first plane, and wherein at least two of said plurality of tines extend from said guide tip from a point below a second plane orthogonal to said first plane.

48. A lead as defined in claim 47 wherein said plurality of tines consists of four tines.

49. A lead as defined in claim 41 wherein said fixation means comprises a plurality of circumferential grooves formed in said guide tip.

50. A lead as defined in claim 41 wherein said fixation means comprises a plurality of longitudinal grooves formed in said guide tip.

51. A lead as defined in claim 41 wherein said fixation means comprises a continuous spiral groove formed in said guide tip.

52. A lead as defined in claim 41 wherein said fixation means comprises at least one through-hole extending entirely through said guide tip.

53. A lead as defined in claim 41 wherein said fixation means comprises a first through-hole extending entirely through said guide tip and a second through-hole extending entirely through said guide tip.

54. A lead as defined in claim 53 wherein said first and second through-holes are orthogonal to each other.

55. A lead as defined in claim 54 wherein said first and second through-holes are intersecting.

56. A lead as defined in claim 41 wherein said fixation means comprises a longitudinal bore formed in said guide tip.

57. A lead as defined in claim 56 wherein said fixation means further includes a through-hole extending entirely through said guide tip and intersecting said longitudinal bore.

58. A lead as defined in claim 41 wherein said fixation means comprises an irregular surface of said guide tip.

* * * * *